(12) United States Patent
Rothenfusser et al.

(10) Patent No.: US 7,057,176 B2
(45) Date of Patent: Jun. 6, 2006

(54) SYSTEM AND METHOD FOR MULTIPLE MODE FLEXIBLE EXCITATION IN SONIC INFRARED IMAGING

(75) Inventors: Max J. Rothenfusser, Munich (DE); Joachim F. Baumann, Munich (DE); Robert E. Shannon, Oviedo, FL (US); Paul J. Zombo, Cocoa, FL (US)

(73) Assignee: Siemens Power Generation, Inc., Orlando, FL (US)

( * ) Notice: Subject to any disclaimer, the term of this patent is extended or adjusted under 35 U.S.C. 154(b) by 0 days.

(21) Appl. No.: 11/069,242

(22) Filed: Mar. 1, 2005

(65) Prior Publication Data

US 2005/0167596 A1 Aug. 4, 2005

Related U.S. Application Data

(63) Continuation of application No. 10/647,569, filed on Aug. 25, 2003.

(60) Provisional application No. 60/453,431, filed on Mar. 10, 2003, provisional application No. 60/407,207, filed on Aug. 28, 2002.

(51) Int. Cl.
  *G01N 21/00* (2006.01)
  *G01N 3/32* (2006.01)
  *G01F 23/00* (2006.01)
  *G01H 13/00* (2006.01)

(52) U.S. Cl. ............... 250/341.6; 250/358.1; 73/601; 73/579; 73/583

(58) Field of Classification Search ............ 250/341.6, 250/341.1, 342, 334, 330, 358.1; 73/601, 73/579, 583
See application file for complete search history.

(56) References Cited

U.S. PATENT DOCUMENTS

| | | | |
|---|---|---|---|
| 3,599,477 A | | 8/1971 | Cohen et al. |
| 3,756,071 A | | 9/1973 | Dory |
| 3,861,200 A | | 1/1975 | Dory |
| 4,174,635 A | | 11/1979 | Oldendorf |
| 4,266,185 A | * | 5/1981 | Charlesworth et al. ..... 324/718 |
| 4,345,457 A | * | 8/1982 | Kuroki et al. ............... 73/37.5 |
| RE32,166 E | * | 6/1986 | Berge ........................... 451/6 |
| 4,607,341 A | | 8/1986 | Monchalin |
| 4,936,649 A | * | 6/1990 | Lymer et al. ................. 385/13 |

(Continued)

FOREIGN PATENT DOCUMENTS

DE 4203272 8/1993

(Continued)

OTHER PUBLICATIONS

Han et al.; "Acoustic Chaos and Sonic Infrared Imaging;" American Institute of Physics; vol. 81, No. 17; Oct. 21, 2002; USA.

(Continued)

*Primary Examiner*—David Porta
*Assistant Examiner*—Faye Polyzos
(74) *Attorney, Agent, or Firm*—John A. Miller; Warn, Hoffmann, Miller & LaLone, P.C.

(57) ABSTRACT

A defect detection system for thermally imaging a structure that has been energized by a sound energy. The system includes a transducer that couples a sound signal into the structure, where the sound signal causes defects in the structure to heat up. In one embodiment, the sound signal has one or more frequencies that are at or near an eigenmode of the structure.

20 Claims, 10 Drawing Sheets

U.S. PATENT DOCUMENTS

| | | | |
|---|---|---|---|
| 5,461,921 A | | 10/1995 | Papadakis et al. |
| 5,493,511 A | * | 2/1996 | Wincheski et al. ............ 702/39 |
| 5,633,468 A | | 5/1997 | Powers et al. |
| 5,763,786 A | | 6/1998 | Camplin et al. |
| 5,810,477 A | * | 9/1998 | Abraham et al. ............... 374/7 |
| 6,232,701 B1 | | 5/2001 | Schuh et al. |
| 6,236,049 B1 | | 5/2001 | Thomas et al. |
| 6,274,967 B1 | | 8/2001 | Zumstrull et al. |
| 6,399,948 B1 | | 6/2002 | Thomas et al. |
| 6,437,334 B1 | | 8/2002 | Thomas et al. |
| 6,593,574 B1 | | 7/2003 | Thomas et al. |
| 6,622,560 B1 | | 9/2003 | Song et al. |
| 6,759,659 B1 | * | 7/2004 | Thomas et al. .......... 250/341.6 |
| 2002/0018510 A1 | * | 2/2002 | Murphy et al. ............... 374/45 |
| 2002/0121602 A1 | | 9/2002 | Thomas et al. |
| 2002/0172410 A1 | | 11/2002 | Shepard |
| 2003/0010124 A1 | | 1/2003 | Bates |
| 2003/0014199 A1 | * | 1/2003 | Toomey ...................... 702/56 |
| 2003/0106376 A1 | | 6/2003 | Shirzad et al. |
| 2003/0115963 A1 | | 6/2003 | Song et al. |
| 2004/0089812 A1 | * | 5/2004 | Favro et al. ............. 250/341.6 |

FOREIGN PATENT DOCUMENTS

| | | |
|---|---|---|
| WO | WO 01/53821 A1 | 7/2001 |

OTHER PUBLICATIONS

Yu Solodov et al.; "CAN: an example of nonclassical acoustic nonlinearity in solids;" Elsevier Science B,V.; Ultrasonics 40 (2002) 621-625; Moscow. Russia.

B.A. Korshak et al.; "DC effects, sub-harmonics, stochasticity and 'memory' for contact acoustic non-linearity;" Elsevier Science B.V.; Ultrasonics 40 (2002) 707-713; Moscow, Russia.

Yu Solodov et al.; "Instability, Chaos, and 'Memory' in Acoustic-Wave-Crack Interaction;" The American Physical Society; Physical Review Letters vol. 88, No. 1; Dec. 19, 2001; Moscow, Russia.

N. Krohn et al.; "Nonlinear Vibrometry for Quality Assurance;" American Institute of Physics; Review of Progress in Quantitative Nondestructive Evaluation, vol. 20, ed. 2001; Germany.

Han et al.; "Enhancement of Sonic IR Imaging by Using Chaotic Acoustic Pulses;" Wayne State University; Detroit, Michigan.

Han et al.; "Enhancement of Sonic IR Imaging through the use of Chaotic Acoustic Pulses;" ASNT 12th Annual Research Symposium 2003; Institute for Manufacturing Research, Wayne State University.

* cited by examiner

SYSTEM AND METHOD FOR MULTIPLE MODE FLEXIBLE EXCITATION IN SONIC INFRARED IMAGING

CROSS-REFERENCE TO RELATED APPLICATIONS

This is a Continuation application of U.S. patent application Ser. No. 10/647,569, titled System and Method for Multiple Mode Flexible Excitation and Acoustic Chaos in Sonic Infrared Imaging, filed Aug. 25, 2003, which claims the benefit of U.S. Provisional Application No. 60/453,431, titled System and Method for Acoustic Chaos and Sonic Infrared Imaging, filed Mar. 10, 2003 and U.S. Provisional Application No. 60/407,207, titled System and Method for Acoustic Chaos and Sonic Infrared Imaging, filed Aug. 28, 2002.

BACKGROUND OF THE INVENTION

1. Field of the Invention

This invention relates generally to a system and associated method for detecting defects in a material and, more particularly, to a system and associated method for detecting defects in a material, where the system includes a transducer for coupling a multiple mode flexible excitation signal into the material, and includes a thermal imaging camera for imaging the heat created in the material as a result of the acoustic chaos or flexible excitation.

2. Discussion of the Related Art

Maintaining the structural integrity of certain structures is very important in many fields because of safety concerns, downtime, cost, etc. Loss of structural integrity is typically caused by material defects, such as cracks, delaminations, disbonds, corrosion, inclusions, voids, etc., that may exist in the structure. For example, it is very important in the power generation industry that reliable techniques are available to examine the structural integrity of turbine, generator and associated balance of plant equipment to ensure the components and systems do not suffer failure during operation. Similarly, it is very important in the aviation industry that reliable techniques are available to examine the structural integrity of the aircraft skin and structural components of the aircraft to ensure that the aircraft does not suffer structural failure when in flight. The structural integrity of turbine blades and rotors and vehicle cylinder heads is also very important in those industries. The most common method for detection of a crack or defect is visual examination by skilled personnel. But, it is known that cracks or defects that may affect the integrity of structural components may not be readily visible without the use of special techniques to aid the examiner. Therefore, various techniques have been developed in the art for the non-invasive and non-destructive analysis of different structural components and materials in many industries.

One known technique for the non-invasive and non-destructive testing of a material for defects includes treating the material with a dye penetrant so that the dye enters any crack or defect that may be present in the material. The material is then cleaned and treated with a powder that causes the dye that remains in the crack to wick into the powder. An ultraviolet (UV) light source is used to inspect the material to observe locations in the material that fluoresce as a result of the dye. This technique has the disadvantage, however, that it is highly inspector intensive and dependent because the person inspecting for the fluorescence must be skilled. Additionally, the dye does not penetrate tightly closed cracks or cracks that are not on the surface of the material.

A second known technique for inspecting a component for defects employs an electromagnetic coil to induce eddy currents in the component. The coil is moved around on the component, and the eddy current pattern changes at a crack or other defect. The complex impedance in the coil changes as the eddy current changes, which can be observed on an oscilloscope. This technique has the drawback, however, that it is also very operator intensive, and is also extremely slow and tedious.

Another known technique for detecting defects in a component employs thermal imaging of the component to identify the defects. In other thermal imaging techniques, a heat source, such as a flash lamp or a heat gun, is used to direct a planar pulse of heat to the surface of the component. The component absorbs the heat, and emits radiation in the infrared wavelengths. Certain types of defects will cause the surface temperature to cool at a different rate around the defect than for the surface temperature of surrounding areas. A thermal or infrared imaging camera is used to image the component and detect the resulting surface temperature variations. Although this technique has been successful for detecting disbonds and corrosions, it is ordinarily not successful for detecting vertical cracks in the component, that is, those cracks that are perpendicular to the surface of the component. This is because a fatigue crack looks like a knife edge to the planar heat pulse, and therefore no, or minimal, heat reflections occur from the crack making it difficult or impossible to see in a thermal image.

Thermal imaging for detecting defects in a material has been extended to systems that employ ultrasonic excitation of the material to generate the heat. An acoustic thermal effect occurs when sound waves propagate through a solid body that contains a crack or other defect causing it to vibrate. Because the faces of the crack ordinarily do not vibrate in unison as the sound waves pass, dissipative phenomena, such as friction between the faces, will convert some of the vibrational energy to heat. By combining this heating effect with infrared imaging, a very efficient, non-destructive crack detection system can be realized. Such imaging systems are generally described in the literature as sonic IR, thermosonic, acoustic thermography, etc.

The article Rantala, J., et al. "Lock-in Thermography with Mechanical Loss Angle Heating at Ultrasonic Frequencies," Quantitative Infrared Thermography, Eurotherm Series 50, Edizioni Ets Piza 1997, pgs. 389–393 discloses such a defect detection technique. The ultrasonic waves cause the opposing edges of the crack to rub together causing the crack to heat up. Because the undamaged part of the component is only minimally heated by the ultrasonic waves, the resulting thermal images of the component show the crack as a bright area against a dark background field.

U.S. Pat. No. 6,236,049 issued May 22, 2001 to Thomas et al. titled "Infrared Imaging of Ultrasonically Excited Subsurface Defects in Materials," assigned to the Assignee of this application, and herein incorporated by reference, discloses a thermal imaging system for detecting cracks and other defects in a component by ultrasonic excitation. An ultrasonic transducer is coupled to the component, and ultrasonic energy from the transducer causes the defects to heat up, which is detected by a thermal camera. The ultrasonic energy is in the form of a substantially constant amplitude pulse. A control unit is employed to provide timing and control functions for the operation of the ultrasonic transducer and the camera.

SUMMARY OF THE INVENTION

In accordance with the teachings of the present invention, a system and method is disclosed for thermal imaging subsurface cracks and other defects in a structure that have been heated by sound energy. A sound source, such as a transducer, couples a sound signal into the structure, where the sound waves in the signal cause the edges of the defects to vibrate against each other and heat up. A thermal imaging camera images the structure when it is being heated by the sound source to identify the defects.

In one embodiment, the sound signal includes a combination of frequencies selected for the particular structure so that the frequency occurs or doesn't occur at or near an eigen-mode of the structure. In this embodiment, the sound source can generate a combination of signals centered at different frequencies, a chirp-signal, a pulse-envelope signal, etc., to vary the sound signal in frequency, amplitude and duration so that the eigen-mode is excited or avoided for flexible multiple mode excitation.

Additional advantages and features of the present invention will become apparent from the following description and appended claims, taken in conjunction with the accompanying drawings.

DETAILED DESCRIPTION OF THE EMBODIMENTS

The following description of the embodiments of the invention directed to a defect detection system for detecting defects in a structure is merely exemplary in nature, and is in no way intended to limit the invention or its applications or uses.

Figure 1:
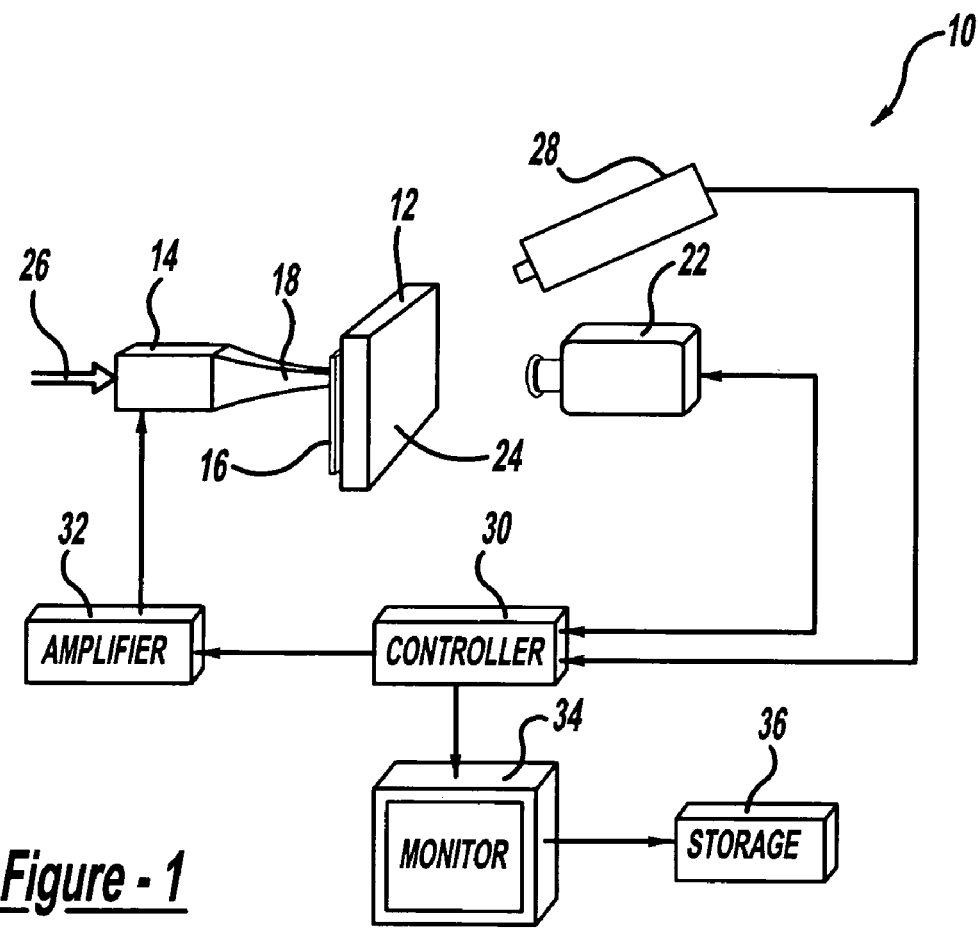
FIG. 1 is a block diagram of a defect detection system, according to an embodiment of the present invention.

FIG. 1 is a block diagram of a defect detection system 10, according to an embodiment of the present invention. The system 10 is being used to detect defects, such as cracks, corrosion, delaminations, disbonds, etc., in a component 12. The component 12 is intended to represent any structural component or material, such as an aircraft skin, turbine blade, turbine rotor, power generator, vehicle cylinder head, etc., that may include these types of defects that could cause catastrophic failure. It is stressed that the component 12 does not need to be metal, but can be other materials, such as ceramics, composites, etc.

The system 10 includes an ultrasonic transducer 14 that generates a sound signal within a certain ultrasonic frequency band. The ultrasonic transducer 14 includes a horn 18 that couples the sound signal into the component 12. The transducer 14 can be a conventional transducer suitable for the purposes of the thermosonic process of the present invention. The transducer 14 provides a transformation of electrical pulses into mechanical displacement by use of a piezoelectric element. For example, the transducer 14 may employ a PZT stack of piezoelectric crystals that are cut to precise dimensions and operate at a very narrow frequency as dictated by the cut dimension of the crystals. The PZT stack is mechanically coupled to the horn 18, and the tip of the horn 18 is pressed against the component 12. Because the tip has a fixed dimension and is inflexible, it exhibits a wide contact area and pressure within the area of contact. This is further influenced by a non-flat, non-smooth surface of the component 12. The transducer 14 can also be a tunable piezo-mechanical exciter, such as those described in U.S. Pat. Nos. 6,232,701 and 6,274,967, or the model F7-1 piezoelectric shaker system manufactured by Wilcox Research of Gaithersburg, Md.

In one embodiment, the transducer 14 generates pulses of ultrasonic energy at a frequency of about 40 kHz for a period of time of about ½ of a second and a power level of about 800 watts. However, as will be appreciated by those skilled in the art, other ultrasonic or sonic frequencies, power levels and pulse durations can be used within the scope of the present invention. The transducer 14 can be the 800 W Branson 40 kHz power supply driving an ultrasonic welding transducer.

Figure 2:
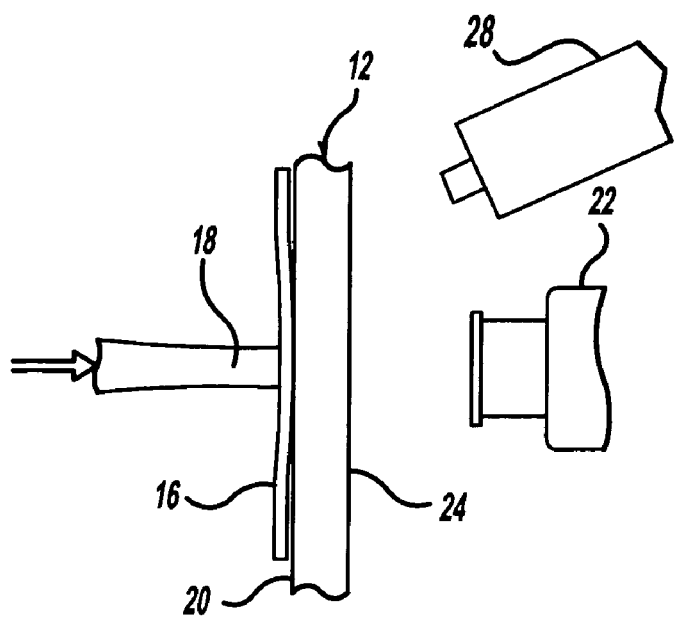
FIG. 2 is a broken-away, side view of a portion of the defect detecting system shown in FIG. 1.

The ultrasonic energy from the transducer 14 is coupled into the component 12 through a mechanical coupler 16. The coupler 16 is in mechanical contact with the transducer horn 18 and a front side 20 of the component 12. FIG. 2 is a broken-away, side view showing the horn 18 in contact with the coupler 16 and the component 12. In one embodiment, the coupler 16 is a non-linear coupler, such as an automotive gasket material, leather, duct tape, cork, Teflon, paper, etc., that helps create acoustic chaos, discussed below, within the component 12 around the defect as a result of the acoustic energy. In other embodiments, the coupler 16 can be a thin piece of a soft metal, such as copper, to effectively couple the ultrasonic energy into the component 12. It is noted, however, that the coupler 16 may not be required in certain applications, and yet still provide acoustic chaos. A force 26 is applied to the transducer 14 by any suitable device (not shown) to push the horn 18 against the coupler 16 and the component 12. The amount of the force 26 applied to the transducer 14 is selected to further enhance the generation of acoustic chaos within the component 12.

The detection system 10 includes a thermal imaging camera 22 spaced a predetermined distance from the component 12, as shown. The camera 22 generates images of the component 12 in conjunction with the ultrasonic excitation of the component 12. The camera 22 can be spaced from a back side 24 of the component 12 at any distance that is suitable to provide images of as much of the component 12 as desired in a single image to simultaneously detect multiple defects with the desired resolution. In other embodiments, the ultrasonic energy from the transducer 14 and the image generated by the camera 22 can be provided at the same side of the component 12 or any side of the component 12. The thermal camera 22 can be any camera suitable for the purposes described herein, such as the Radiance HS camera available from Raytheon or the Indigo Systems Phoenix IR camera. In one embodiment, the camera 22 senses infrared emissions in a 3–5 micron wavelength range, and generates images at 100 frames per second. The camera 22 may include a focal plane array having 256×256 InSb pixels to generate the desirable resolution.

A controller 30 provides timing between the transducer 14 and the camera 22. The controller 30 can be any computer suitable for the purposes described herein. When the detection process is initiated, the controller 30 causes the camera 22 to begin taking sequential images of the component 12 at a predetermined rate. Once the sequence of images begins, the controller 30 sends a signal to a power amplifier 32 that causes the amplifier 32 to send a pulse to the transducer 14 to generate the pulsed ultrasonic signal. The ultrasonic energy is in the form of a simple pulse at the desired frequency. The image is generated by the camera 22 and sent to a monitor 34 that displays the images of the component 12. The images can also be sent to a storage device 36 to be viewed at another location if desirable.

The ultrasonic energy applied to the component 12 causes the faces of cracks and other defects in the component 12 to rub against each other and create heat. By providing the proper parameters in the system 10, as discussed herein, acoustic chaos is created in the component 12 to enhance the heating of the defect. The heat appears as bright spots in the images generated by the camera 22. Therefore, the system 10 is good at identifying very small tightly closed cracks. For those cracks that may be open, where the faces of the crack do not touch, the heat is generated at the stress concentration point at the crack tip. This point appears as a bright spot on the images indicating the end or tip of an open crack. The ultrasonic energy is effective to heat the crack or defect in the component 12 regardless of the orientation of the crack relative to the energy pulse. The camera 22 takes an image of the surface of the component 12 providing a visual indication of any crack in the component 12 no matter what the position of the crack within the thickness of the component 12.

As will be discussed in more detail below, the ultrasonic energy from the transducer 14 generates acoustic chaos in the component 12. The acoustic chaos can be measured by measuring the vibration of the component 12 to determine the chaos frequencies. In one embodiment, a vibrometer 28, such as the Polytec PI OFV-511 single fiber Doppler laser vibrometer, can be used to measure the vibrations of the component 12. The vibrometer 28 emits an optical beam towards the component 12, and optical reflections therefrom are received by the vibrometer 28. The time of travel of the optical signal to the component 12 and back determines how close the component 12 is to the vibrometer 28, and thus its vibration. The vibrometer 28 uses the doppler effect and suitable algorithms to calculate the vibration frequencies. The measurements made by the vibrometer 28 are sent to the controller 30 and displayed as frequency signals on the monitor 34. The controller 30 Fourier transforms the signals from the vibrometer 28 to generate the frequency signals that are time dependent on the vibration spectra. In one embodiment, the vibrometer 28 has a digitizing rate up to 2.56 MHz, so that vibrational frequencies up to about 1.2 MHz can be determined. It is noted that the vibrometer 28 does not necessarily have to be aimed normally at the component 12.

In an alternate embodiment, the vibrometer 28 can be replaced with a microphone that simply measures the audible frequencies, or the horn "screech," when the transducer 14 emits the ultrasonic pulse. It is believed that the horn screech itself is an indication that acoustic chaos is occurring in the component 12. The signals received by the microphone are also sent to the controller to be displayed on the monitor 34.

Figure 3A:
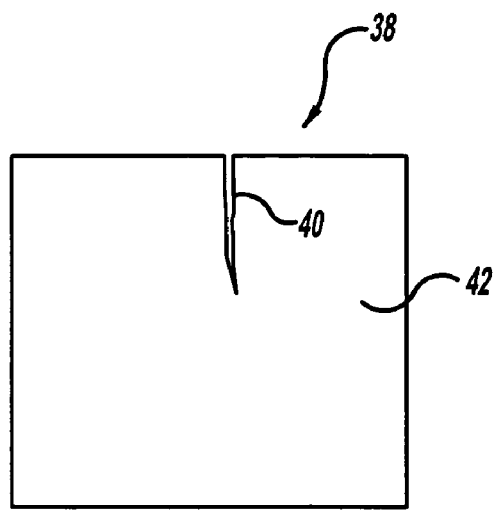
FIGS. 3(A)–3(D) show consecutive images at predetermined time intervals of an open crack in a component that has been ultrasonically excited and thermally imaged by the defect detection system of the present invention.
Figure 3B:
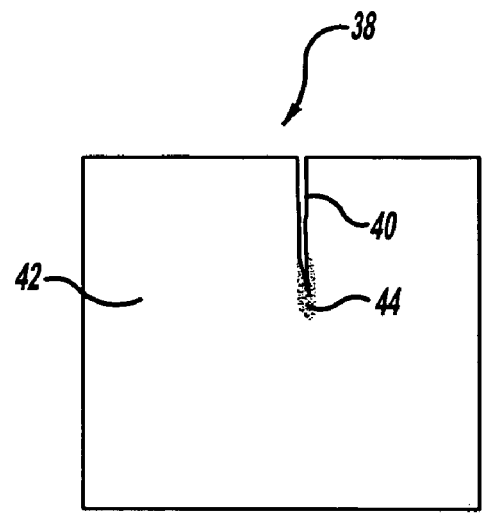
Figure 3C:
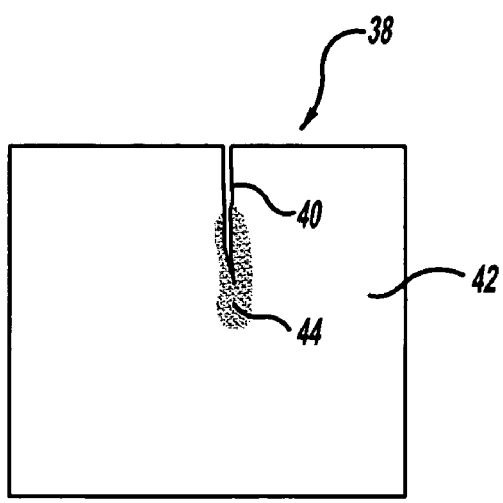
Figure 3D:
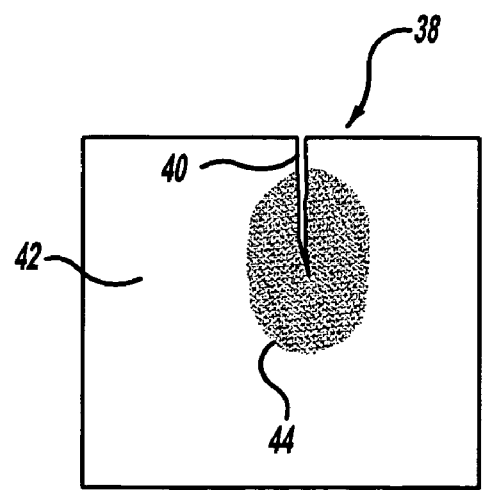

To illustrate the process of imaging a crack in a component as discussed herein, FIGS. 3(A)–3(D) show four sequential images 38 of an open fatigue crack 40 in a structure 42. FIG. 3(A) shows the image 38 of the structure 42 prior to the ultrasonic energy being applied. FIG. 3(B) shows the image 38 of the structure 42 about 14 ms after the ultrasonic energy is applied. As is apparent, a light (higher temperature) spot 44 (sketched as a dark region) appears at the closed end of the crack 40, where mechanical agitation causes the heating. FIGS. 3(C) and 3(D) show subsequent images 38 at times of about 64 ms and 114 ms, respectively. The light spot 44 on the image 38 increases dramatically over this sequence, clearly indicating the location of the crack 40.

According to another embodiment of the present invention, the transducer 14 can be replaced with an electromagnetic acoustic transducer (EMAT). An EMAT used for this purpose is disclosed in U.S. Pat. No. 6,399,948 issued to Thomas et al., assigned to Wayne State University and Siemens Westinghouse Power Corporation, and herein incorporated by reference.

An EMAT includes a permanent magnet, or electromagnet, that generates a static magnetic field in the object being tested. An electromagnet is provided that would be energized with a time-varying current to generate eddy currents on and just beneath the surface of the object being tested. The eddy currents interact with the static magnetic field to generate a Lorentz force that acts on free electrons in the object, which induce collisions with ions in the object in a direction mutually perpendicular to the direction of the static magnetic field and the local eddy currents. This interaction generates sound waves of various polarizations that are reflected off of discontinuities in the object to identify defects. In the present invention, these sound waves generate heat at the defect site. The sound waves can be in various forms, including, but not limited to sheer waves, surface waves, plate waves, Raleigh waves, lamb waves, etc. In order to generate the acoustic chaos as discussed herein and transmit a chaotic waveform, the EMAT cannot be tuned to a specific resonant frequency, but should be broadband.

Figure 4:
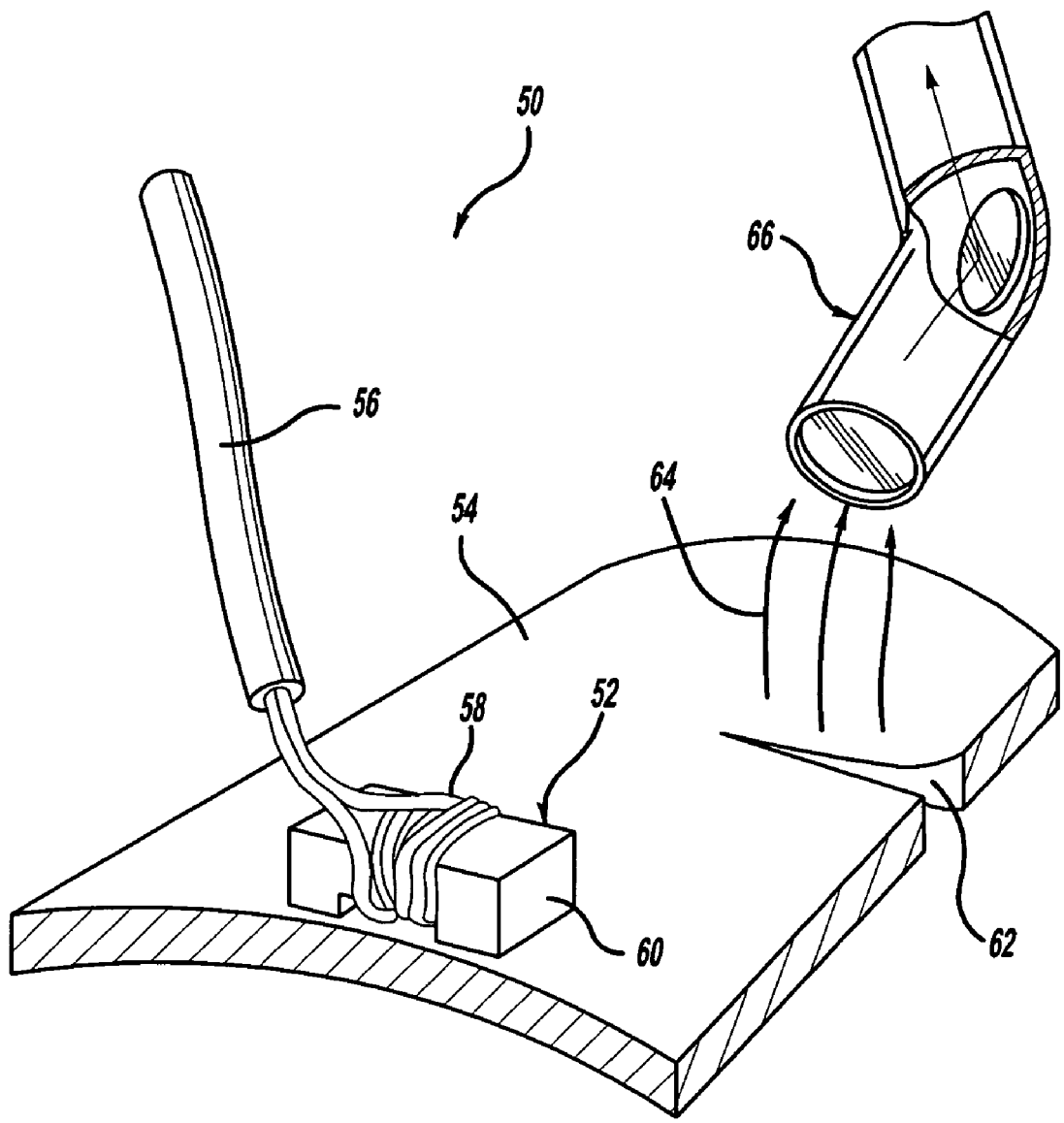
FIG. 4 is a plan view of a defect detection system employing an electromagnetic acoustic transducer, according to another embodiment of the present invention.

To illustrate this embodiment of the present invention, FIG. 4 is a broken-away, perspective view of a defect detection system 50 employing an EMAT 52 of the type discussed above. The EMAT 52 is positioned against a turbine blade 54 inside of a turbine engine, but can be any suitable part being detected for defects. A length of cable 56 is coupled to the EMAT 52 and a controller (not shown), such as the controller 30 above. The cable 56 includes a coil 58 wrapped around a permanent magnet 60. An AC voltage signal on the cable 56 applied to the coil 58 causes eddy currents to interact with the static magnetic field generated by the permanent magnet 60 in the turbine blade 54. The interaction of the eddy currents and the static magnetic field generates sonic or ultrasonic waves that cause the faces of a crack 62 in the blade 54, or other defect, to rub against each other and generate heat radiation 64. A radiation-collecting device 66 is coupled to a suitable infrared camera (not shown), such as the camera 22, to provide the images.

A coupling material may be provided between the permanent magnet 60 and the turbine blade 54 to effectively couple the electromagnetic energy from the EMAT 52 into the turbine blade 54. The coupling material could be part of the permanent structure of the magnet 60 to make the system 50 more applicable for remote detection inside of a turbine engine. Because the EMAT 52 can be made broadband, the chaos would be created in the turbine blade 54 by applying an electrically generated chaos signal as discussed below.

According to the invention, acoustic chaos is created in the component 12, which acts to increase the amount of thermal energy at the defect in the component 12 above that which would be generated in the absence of acoustic chaos. Acoustic chaos is defined herein as a range of frequencies providing a vibrational waveform whose spectral frequencies are related to the excitation frequency (here 40 kHz) by the ratios of rational numbers. The frequencies associated with acoustical chaos can be both lower and higher than the excitation frequency. Acoustic chaos can be modeled as a mathematical relationship, and has been well documented in the literature. One such example can be found in Rasband," S. Neil, et al., "Chaotic Dynamics of Non-Linear Systems," (1990).

To generate acoustic chaos in the component 12, the correct combination of the force 26 applied to the transducer 14, the material of the coupler 16, the thickness of the coupler 16, the frequency of the acoustic input pulse and the duration of the acoustic input pulse must be provided. A 40 kHz acoustic pulse is beyond normal adult hearing. However, it has been observed that the best image quality from the camera 22 occurs if an acoustic sound, or "horn screech" is sensed. The presence of this audible screech is ordinarily attributed to non-linearities in the coupling between the horn 18 and the component 12. It has been discovered, however, that this horn screech occurs as a result of anharmonic frequencies resulting from the onset of acoustic chaos or from pseudo-chaotic conditions that precede acoustic chaos.

Various materials that exhibit non-linear characteristics are suitable for the coupler 16. The coupler 16 is compressed by the force 26 applied to the transducer 14 to keep the horn 18 in place against the component 12, and provide a tight contact. However, it has been observed that the amount of the force 26 applied to the transducer 14 helps obtain the desired screech, and thus a higher quality image. If the force is too little, then very little sound is coupled into the component 12. The same affect occurs if the force 26 is too great. The exact amount of force necessary to produce the screech depends upon the particular acoustic horn being used to inject the sound, presumably because different horns have different vibration amplitudes. Thus, a particular combination of vibration amplitude and applied force is crucial to generating the screech.

It is possible that the proper force applied to the horn 18 will allow the tip of the horn 18 to recoil from the surface of the component 12 during the negative half of the acoustic period of the input pulse. If such a recoil occurs, the input to the component 12 will be more like a series of equally spaced kicks or bumps at the ultrasonic input frequency, than a sinusoidal wave. When the system being kicked has natural resonances, it is likely that one or more of these resonances will be excited by the kicks. The solution of the mathematical problem of a resonant system that is subject to a series of regularly spaced kicks can be found in the book referenced above. After the nth kick, the solution is:

$$X_n = A_n \cos \omega n \, \tau + B_n \sin \omega n \, \tau, \quad (1)$$

where the coefficients $A_n$ and $B_n$ are given by:

$$A_n = A_1 + \frac{C}{\omega} \sin\pi n\left(\frac{\omega}{\Omega}\right)\left[\cos\pi n\left(\frac{\omega}{\Omega}\right) - \cot\pi n\left(\frac{\omega}{\Omega}\right)\sin\pi n\left(\frac{\omega}{\Omega}\right)\right] \quad (2)$$

$$B_n = B_1 + \frac{C}{\omega}\left[\sin\pi n\left(\frac{\omega}{\Omega}\right)\left[\sin\pi n\left(\frac{\omega}{\Omega}\right) + \cot\pi n\left(\frac{\omega}{\Omega}\right)\cos\pi n\left(\frac{\omega}{\Omega}\right)\right] - 1\right] \quad (3)$$

Here, C is the strength of the kick, $\omega$ is the natural frequency of the oscillator, and $\Omega = (2\pi/\tau)$ is the angular "kicking" frequency. When $\omega/\Omega$ is a rational fraction, this set of equations is periodic and the possibility of a resonance exists.

Figure 5:
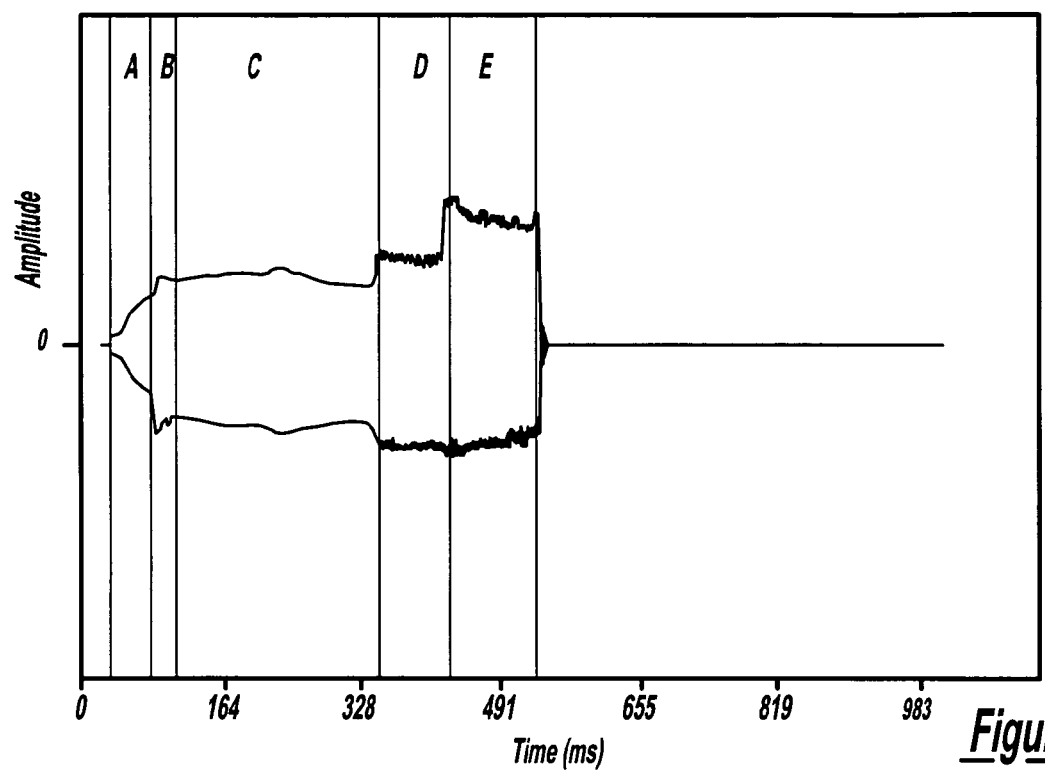
FIG. 5 is a waveform showing the vibrational response of a sample that has been excited by a 40 kHz excitation pulse, where the waveform has been separated into five regions A–E.

To further study the occurrence of acoustic chaos in the component 12 as a result of the application of the ultrasonic signal as discussed herein, vibrational response images of the component 12 can be obtained using, for example, the vibrometer 28. FIG. 5 is a graph with time on the horizontal axis and amplitude on the vertical axis showing the waveform sensed by the vibrometer during the duration of the input pulse. The waveform is separated into five regions, labeled A–E. Each of the separate regions A–E were Fourier analyzed, where the Fourier analysis of region A shows a pure 40 kHz sample vibration. The "bump" in region B suggests a qualitative change in vibrational behavior. In fact, the analysis shows the presence of a strong sub-harmonic signal at 20 kHz, along with all multiples of 20 kHz up to 160 kHz, but with no additional measurable frequencies. Following the "bump" in region B, region C is a long region where Fourier analysis shows no sub-harmonics present, but in which all multiples of 40 kHz are present up to 200 kHz. Thus, in the first three regions A–C, no audible frequencies are present.

Figure 6:
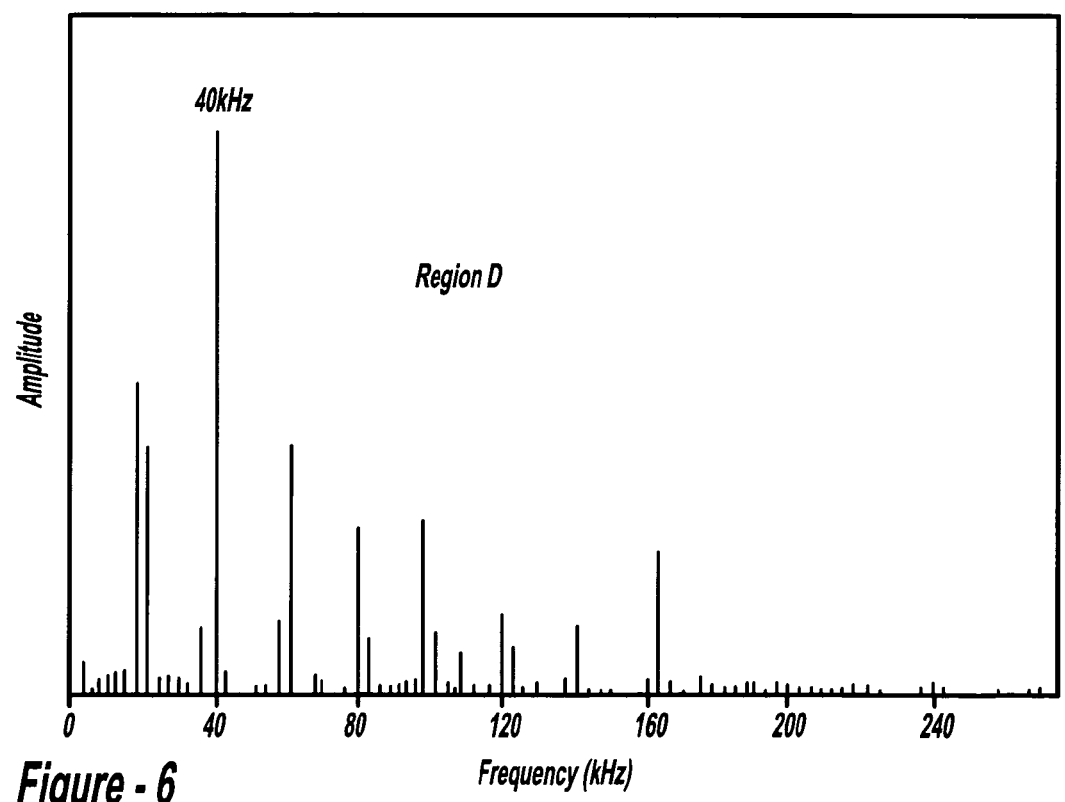
FIG. 6 is a graph with frequency on the horizontal axis and amplitude on the vertical axis showing the frequency peaks generated by acoustic chaos in region D of the waveform shown in FIG. 5.

A dramatic change in the waveform and in its spectrum occurs in regions D and E, and corresponds to the onset of the audible "screech". FIG. 6 is a graph with frequency on the horizontal axis and amplitude on the vertical axis of the Fourier Transform spectrum of region D. As is apparent, region D contains a series of frequencies which are multiples of 1/11th of the fundamental frequency (40 kHz), together with numerous small, unidentified frequencies.

Figure 7:
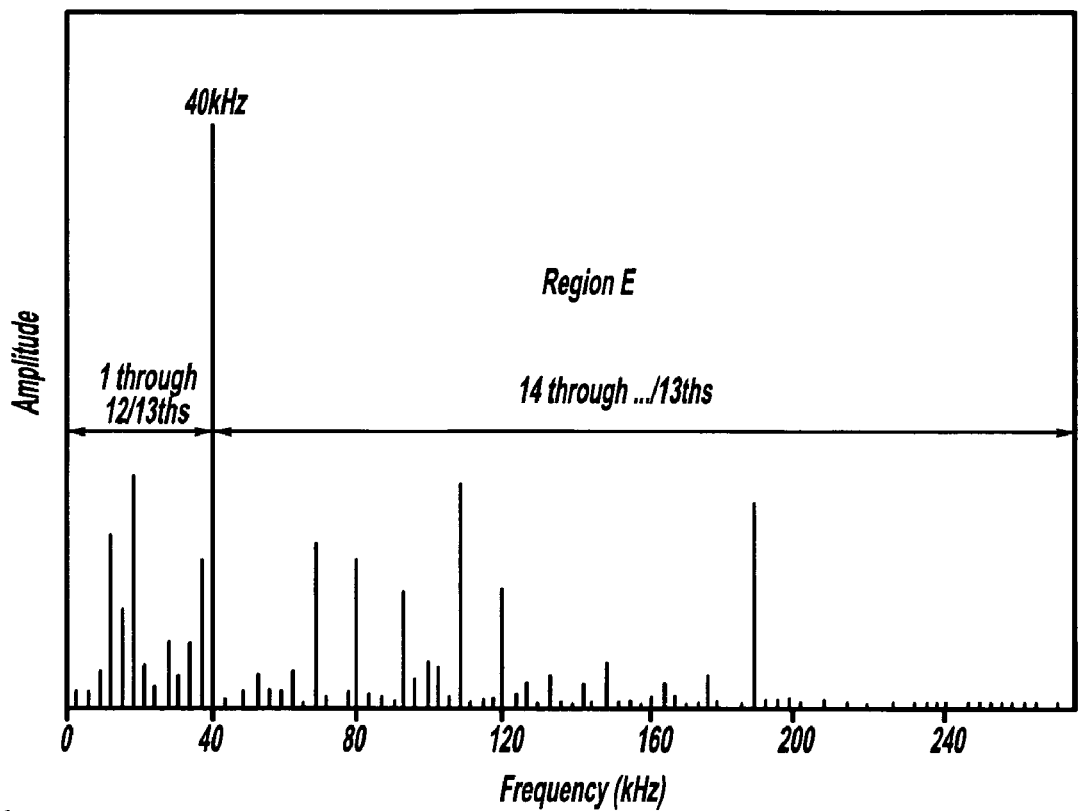
FIG. 7 is a graph with frequency on the horizontal axis and amplitude on the vertical axis showing the frequency peaks generated by acoustic chaos in region E of the waveform shown in FIG. 5.

In region E, another dramatic switch in the waveform occurs, and the Fourier Transform becomes a sequence of frequencies that are multiples of 1/13th of the fundamental frequency (40 kHz), as shown in FIG. 7. In more typical waveforms, there are mixtures of many such sequences, involving fractions such as halves, thirds, fourths, fifths, sevenths, eighths, ninths, elevenths, thirteenths, twenty-fourths, etc. There are clear switches to and among sequences in many of these waveforms where the amplitude increases. Associated with these increases in amplitude and complexity of the waveform are pronounced increases in heating, as shown in the images. The same phenomenon has been observed using different power supplies, transducers, fundamental frequency, etc.

The presence of so many frequencies in the vibrational spectrum is clear evidence of quasi-chaotic excitation as described in equations (1)–(3). Equations (1)–(3) were developed on the basis of a harmonic oscillator being "kicked" by another periodic system. This phenomenon has been observed not only in the case of simple plates, but also with very large, complex-shaped objects, such as a turbine engine fan disk. Thus, it seems likely that the resonant system here is in fact the acoustic horn and associated electronics, so that it may be instructive to think not of the horn "kicking" the sample, but rather of the sample "kicking" the horn.

Figure 8:
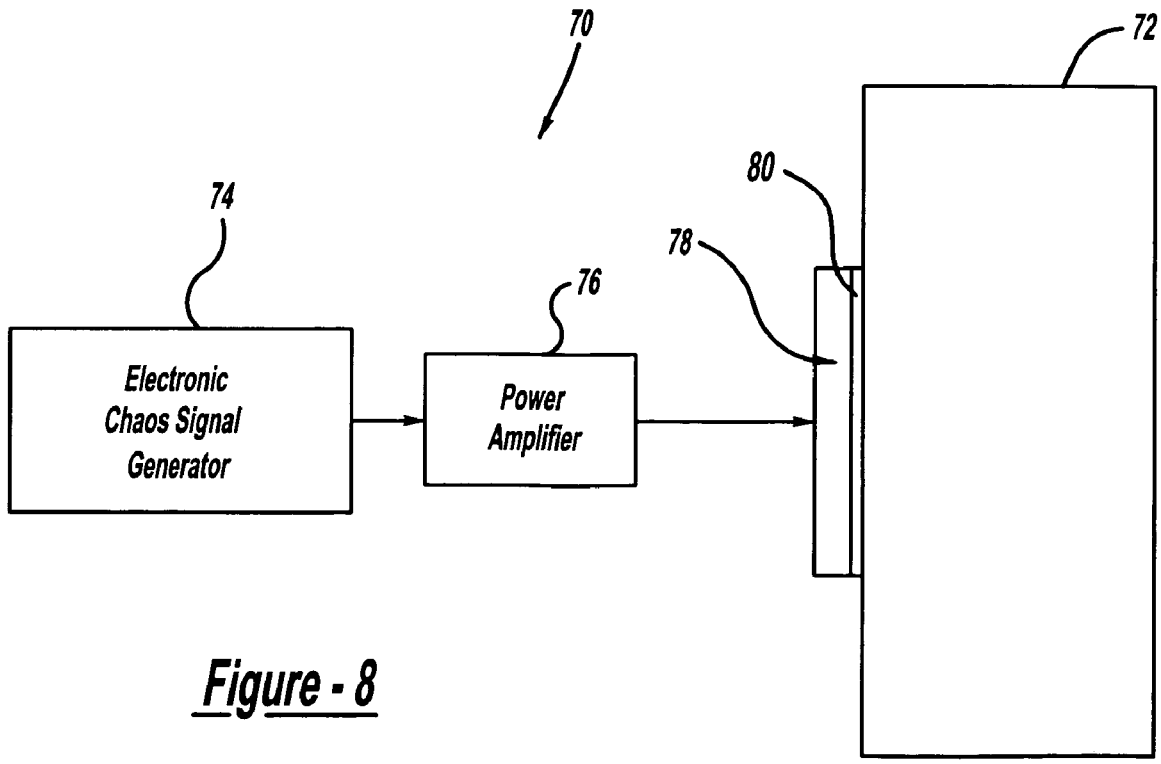
FIG. 8 is a block diagram of an acoustic chaos defect detection system, according to another embodiment of the present invention.

FIG. 8 is a block diagram of a defect detection system 70 that generates acoustic chaos in an object 72 being tested that may or may not have a defect. The object 72 is imaged by a thermal imaging camera (not shown), as discussed above, to determine whether a defect exists. In this embodiment, a chaos signal is generated by an electronic chaos signal generator 74 instead of relying on the force applied to the acoustical horn, the coupling material, the coupler thickness and the frequency and duration of the excitation pulse, as discussed above. The chaos signal generator 74 can be any device that generates a chaos signal of the type being discussed herein. Generally, the generator 74 would include nonlinear circuit elements to create an electrical waveform that has all of the peculiar frequency components of chaotic sound. Alternately, the chaos signal may be able to be generated digitally by a digital computer.

The chaos signal generated by the generator 74 is applied to a power amplifier 76 that amplifies the signal. The amplified chaos signal is applied to a broadband transducer 78. The signal generates a sound signal in the transducer 78 that is coupled into the object 72 through a coupler 80. Because the signal applied to the transducer 78 is already chaotic, it can be linearly coupled into the object 72 by the transducer 78. The acoustic signal from the transducer 78 thus induces acoustic chaos in the object 72 to increase the heating of the defects in the object 72.

According to another embodiment of the present invention, a thermography defect detection system excites an object being inspected with an ultrasonic excitation signal over multiple frequencies to produce heat at the location of cracks and crack-like defects in the object that can be detected by an infrared camera. The object can be any body comprised of solid materials, such as metals, ceramics, plastics, glasses, coated metals, metal matrix composites, ceramic matrix composites and polymer matrix composites.

As is known in the art, eigen-modes and eigen-frequencies exist in an elastic object, which are defined by the object's geometry, elastic properties, additional boundary conditions, such as clamping in the fixture, and the technique of generating vibrations in the object. The eigen-mode of an object defines the frequency that will resonate within the object where vibrations will add. Therefore, the local vibration amplitude in the object, and from this the detectability of defects, may significantly depend on the excitation frequency, amplitude and duration of the excitation signal. An excitation signal with a frequency at or near an eigen-mode of the object results in a substantial increase of the vibrational amplitude in the object. Because the eigen-modes of industrial components are not easily known and can change as a result of small changes in geometry, elastic properties and boundary conditions of the component, sometimes in a nonlinear manner, the use of a single frequency, amplitude and duration excitation signal may lead to unpredictable vibration results. Substantial variations in results have been observed using vibration sources emitting one or more pulses at a predetermined frequency, amplitude or duration.

Stimulation of the object with a set of frequencies or with changing frequencies may be advantageous because more than one eigen-mode in the object can be excited, and therefore the distribution of the vibrations amplitude becomes more even, i.e., the avoidance of nodes. Particularly, the combination of the different strain amplitudes belonging to the corresponding frequencies and mode patterns provides an occurrence of a strain of sufficiently high amplitude and a sufficient number of cycles at any site of the object where defects are detected. This can be done by combining different mode patterns with different natural frequencies. The possibility to select frequencies is helpful in the case where special eigen-modes exist that could damage the object, especially thin parts. The excitation signal could be tuned or adjusted to avoid those frequencies.

Figure 9:
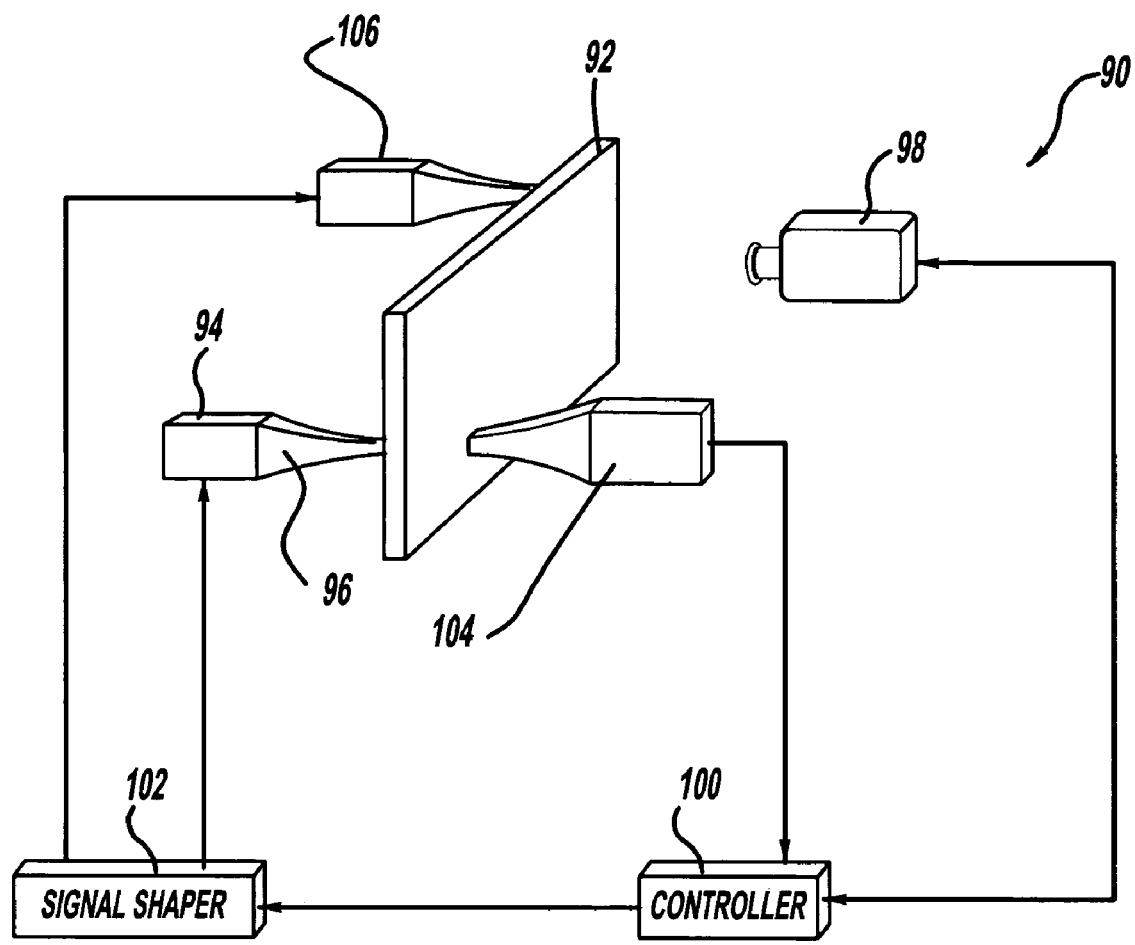
FIG. 9 is a block diagram of a thermography defect detection system, according to another embodiment of the present invention, that is able to provide a flexible multiple mode input signal having selected frequencies to control the frequency, amplitude and duration of the input signal.

FIG. 9 is a block diagram of a thermography defect detection system 90 for detecting defects in an object 92 of the type generally discussed herein. The thermography system 90 includes an ultrasonic transducer 94 having a horn 96 that couples sound energy into the object 92 at certain defined frequency patterns. In other embodiments, the horn 96 can be replaced with a broadband transducer, as will be discussed further below. The transducer 94 can be the same as the transducer 14, or another suitable sound instrument consistent with the discussion herein. For example, the transducer 94 can be a piezoelectric, an electromagnetic or a magneto-strictive element to provide the desired frequency patterns. As will be discussed below, the sound energy coupled into the object 92 is in the form of pulsed frequency signals to heat the defects (cracks) within the object 92. An infrared camera 98 images the defects that are heated to identify them in the object 92.

A controller 100 controls the operation of the system 90, and provides timing between the transducer 94 and the camera 98. The controller 100 controls a signal shaper 102 that provides a signal to the transducer 94 at the desired pulse rate, pulse duration, frequency, envelope shape, etc., consistent with the discussion herein for the various embodiments. The system 90 also includes a vibration sensor 104 positioned against the object 92 that listens to the vibrational modes and patterns within the object 92 when it is being excited by the excitation signal. The vibration sensor 104 can be any sensor suitable for the purposes discussed herein, such as an accelerometer, an eddy current based vibration sensor, an optical vibration sensor, a microphone, an ultrasonic transducer or an ultrasonic vibration sensor. The sensor 104 provides a signal to the controller 100 indicative of the vibration pattern so that the controller 100 knows what vibrations are being induced in the object 92 by the excitation signal. The controller 100 can then use this information to change the signal applied to the signal shaper 102 to vary the excitation signal applied to the object 92 from the transducer 94 to get a different, possibly more desirable, vibration pattern within the object 92 to better heat the defects.

In one embodiment, the transducer 94 is a broad-band transducer that is able to provide frequencies tuned at different center frequencies or a broad-band signal having a relatively large frequency band. The broad-band transducer 94 can provide signals centered at different frequencies sequentially, or at the same time. The frequencies can be provided in an increasing manner or a decreasing manner, randomly, swept up, swept down, random sweep, etc. Providing multiple frequency bands may eliminate dead, or unenergized zones, within the object 92. Also, the excitation signal can be a band of frequencies. Further, the excitation signal can be a chirp-signal whose frequency changes in time.

Alternately, the system 90 can employ multiple transducers tuned at different narrow band center frequencies to excite the object 92 with multiple excitation signals at different frequencies. Thus, the system 90 can employ a second transducer 106 that also couples a sound excitation signal into the object 92, where the transducers 94 and 106 would be tuned to different narrow band frequencies. Further, the system 90 can employ an array of transducers. The controller 100 would control the timing of the excitation signals from the transducers 94 and 106 and the signal shaper 102 would define the shape of the signals generated by the transducers 94 and 106 to get the desirable vibrations within the object 92. Of course, the system 90 could employ more than two transducers for more than two frequency input signals.

Flexible excitation systems, applicable to be used for one or more of the transducer 94, the controller 100 and the signal shaper 102, are known in the art that provide sound and ultrasonic signals. These systems may include suitable arbitrary waveform generators, amplifiers, converters and other related equipment to generate the frequency patterns. These systems allow the creation of arbitrary or specifically designed waveforms composed of selective frequency content and amplitude characteristics by the appropriate mixing of continuous signals or combining of continuous signals and pulse signals, or by specific control of the amplitude of continuous signals. Thus, arbitrary shapes of pulse envelopes and frequency characteristics can be generated. These arbitrary shapes can also be generated digitally by a digital computer or by a digital signal shaper. Further, the system components can be driven dynamically, which allows control of amplitude and frequency based on additional inputs, such as from vibration sensors and accelerometers.

Figure 13:
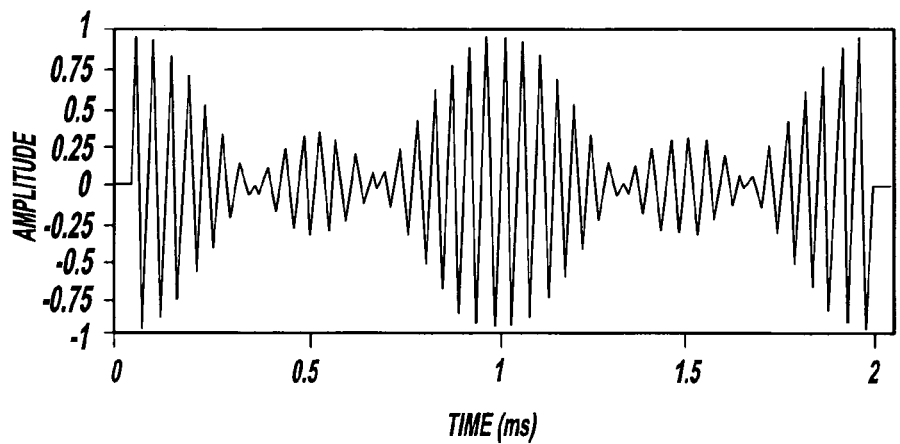
FIG. 13 is a graph with time on the horizontal axis and amplitude on the vertical axis showing part of an input excitation signal for the system shown in FIG. 9 that has three frequencies, where a first frequency is centered at 20 kHz, a second frequency is centered at 21 kHz and a third frequency is centered at 22 kHz.
Figure 14:
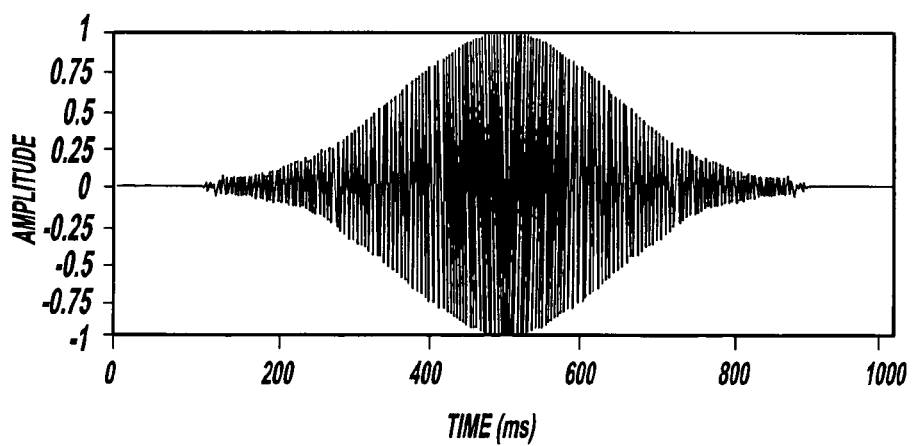
FIG. 14 is a graph with time on the horizontal axis and amplitude on the vertical axis showing an input excitation signal for the system shown in FIG. 9 that is a Gaussian frequency band around 20 kHz.
Figure 15:
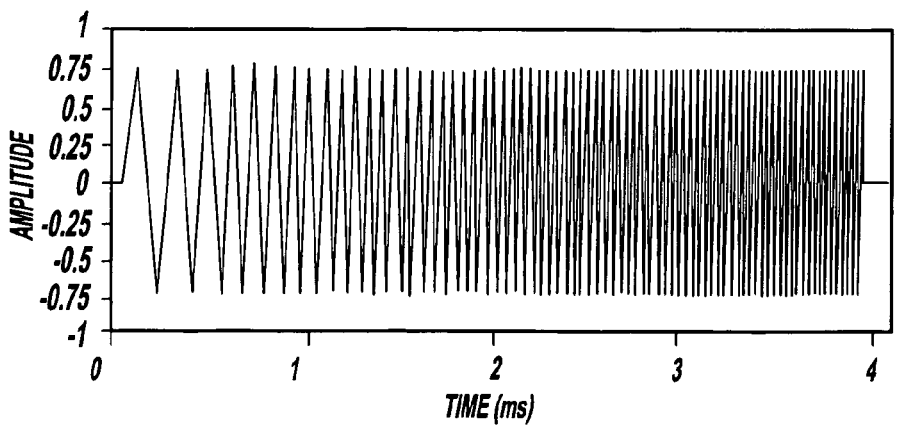
FIG. 15 is a graph with time on the horizontal axis and amplitude on the vertical axis showing an input excitation signal for the system shown in FIG. 9 that is a chirp-signal swept upwards.

FIGS. 10–18 are graphs showing various excitation signals that can be applied to the object 92 having various frequency characteristics for various applications. In one embodiment, the various excitation signals from the transducer 94 are intended to excite the eigen-modes in the object 92 to further increase or enhance the heating of the defects in the object 92. In an alternate embodiment, the excitation signals avoid the eigen-modes in the object 92 to reduce the chance of damaging the object 92. FIGS. 10–13 only show part of the excitation signal over a 2 ms timeframe. FIG. 15 only shows part of the excitation signal over a 4 ms timeframe. Typical durations of the excitation signal for these types of signals can be about 1 second. FIGS. 14 and 16–19 show the total excitation signal.

Figure 10:
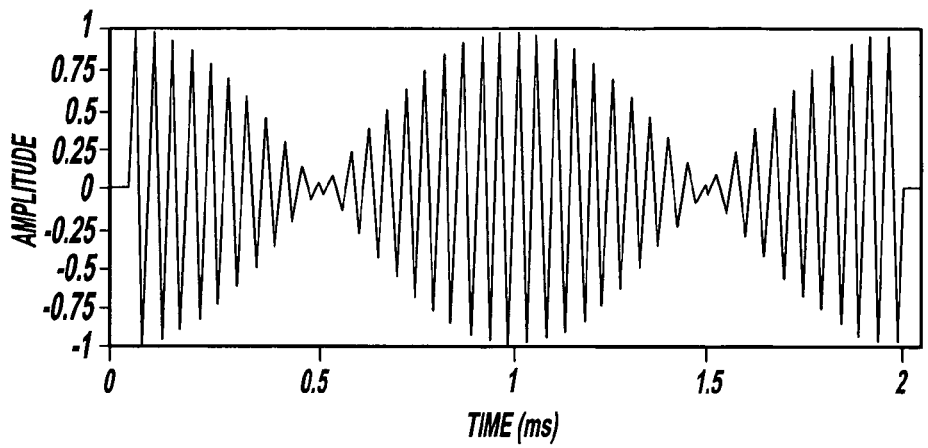
FIG. 10 is a graph with time on the horizontal axis and amplitude on the vertical axis showing part of an input excitation signal for the system shown in FIG. 9 that has two frequencies, where a first frequency is centered at 20 kHz and a second frequency is centered at 21 kHz.
Figure 11:
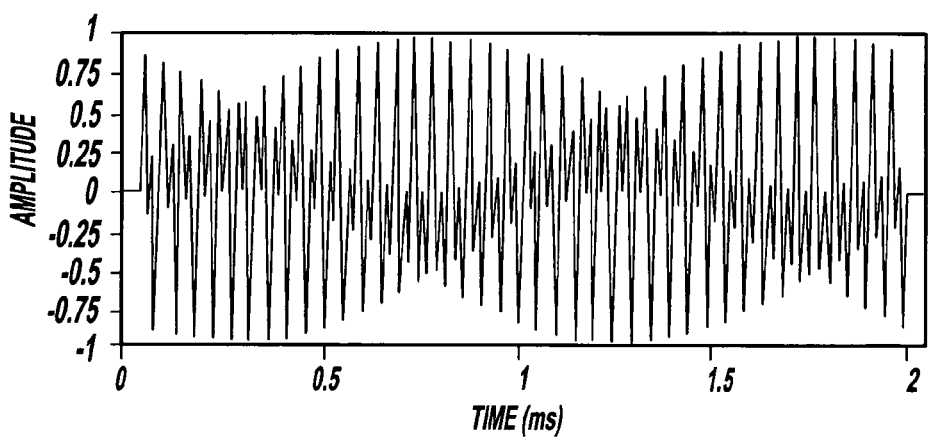
FIG. 11 is a graph with time on the horizontal axis and amplitude on the vertical axis showing part of an input excitation signal for the system shown in FIG. 9 that has two frequencies, where a first frequency is centered at 20 kHz and a second frequency is centered at 40.5 kHz.
Figure 12:
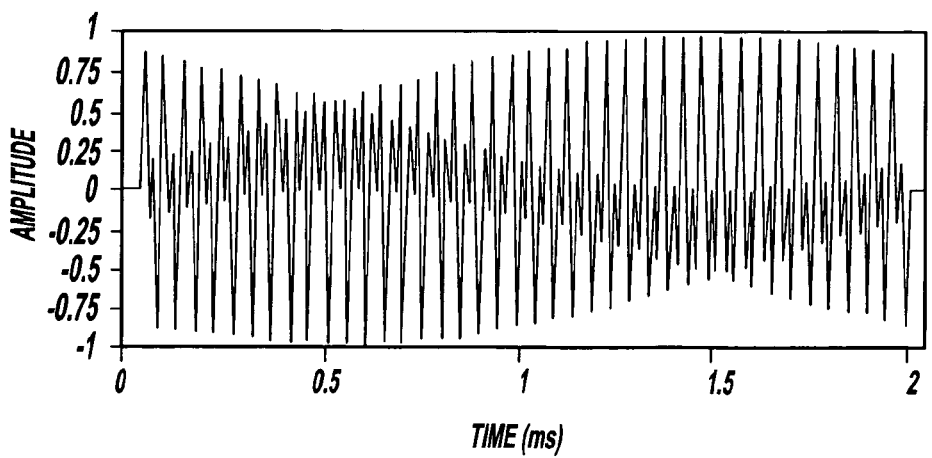
FIG. 12 is a graph with time on the horizontal axis and amplitude on the vertical axis showing part of an input excitation signal for the system shown in FIG. 9 that has two frequencies, where one frequency is centered at 20 kHz and the other frequency is centered at 41 kHz.
Figure 16:
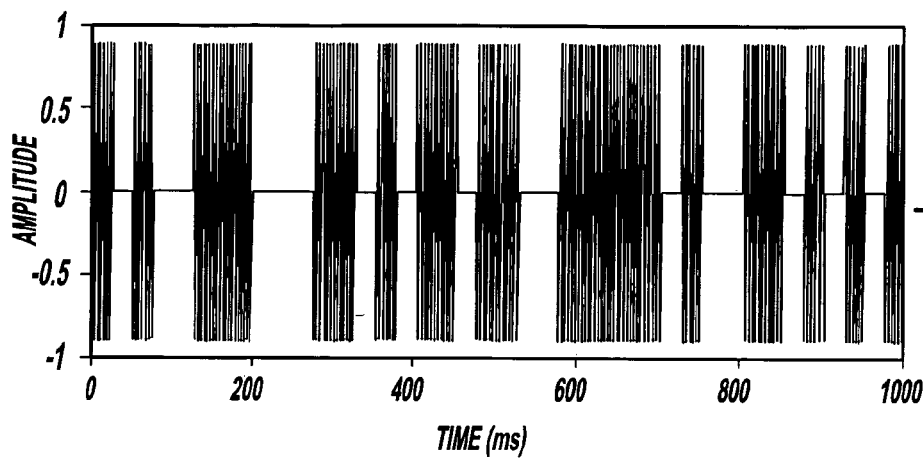
FIG. 16 is a graph with time on the horizontal axis and amplitude on the vertical axis showing an input excitation signal for the system shown in FIG. 9 that is a signature signal having random pulses in a digital sequence.
Figure 17:
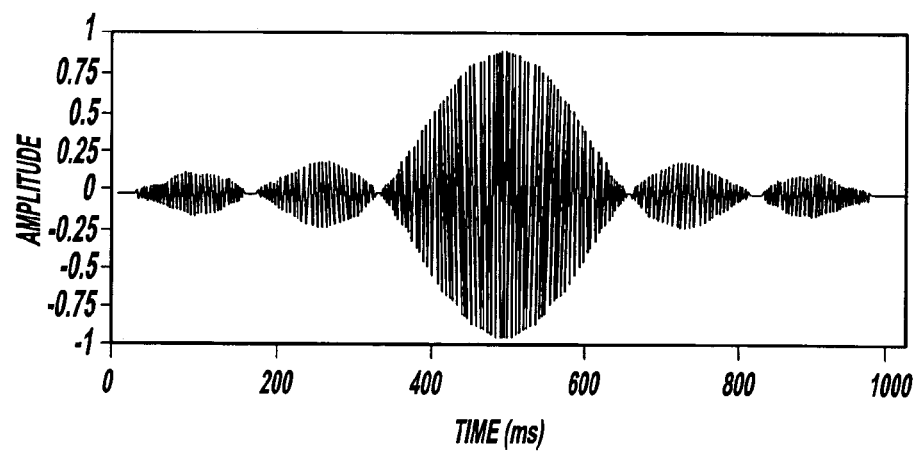
FIG. 17 is a graph with time on the horizontal axis and amplitude on the vertical axis showing an input excitation signal for the system shown in FIG. 9 that is based on a rectangular frequency band centered around 20 kHz.

FIG. 10 shows an excitation signal pulse that is a combination of two frequencies centered at 20 kHz and 21 kHz. FIG. 11 shows an excitation signal pulse that is a combination of two frequencies centered at 20 kHz and 40.5 kHz. FIG. 12 shows an excitation signal pulse that is a combination of two frequencies centered at 20 kHz and 41 kHz. FIG. 13 shows an excitation signal pulse that is a combination of three frequencies centered at 20 kHz, 21 kHz and 22 kHz. FIG. 14 shows an excitation signal pulse that is a Gaussian frequency band around 20 kHz. FIG. 15 shows an excitation signal that is a chirp-signal having a frequency sweep upwards. FIG. 16 shows an excitation signal that is a signature signal defined by a set of random pulses in a digital sequence (1, 0, 1, 0, 0, 1, 1, 1, 0, 0, 1, 1 . . . ) that switch the excitation signal on and off, where the total excitation signal is shown. The random set of pulses can be transferred to the sensed infrared signal and decoded to improve the signal-to-noise ratio. FIG. 17 shows an excitation signal that is based on a rectangular frequency band around 20 kHz, where the total excitation signal is shown.

Figure 18:
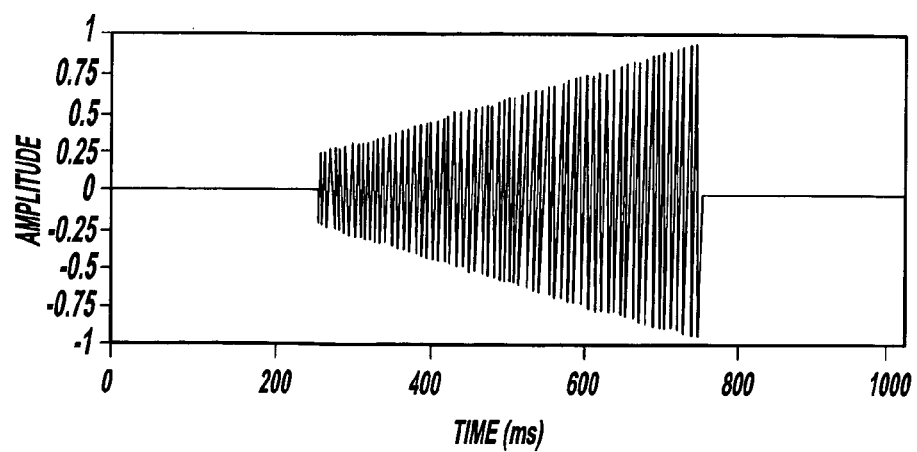
FIG. 18 is a graph with time on the horizontal axis and amplitude on the vertical axis showing an input excitation signal for the system shown in FIG. 9 that has an increasing amplitude with a step at the beginning.
Figure 19:
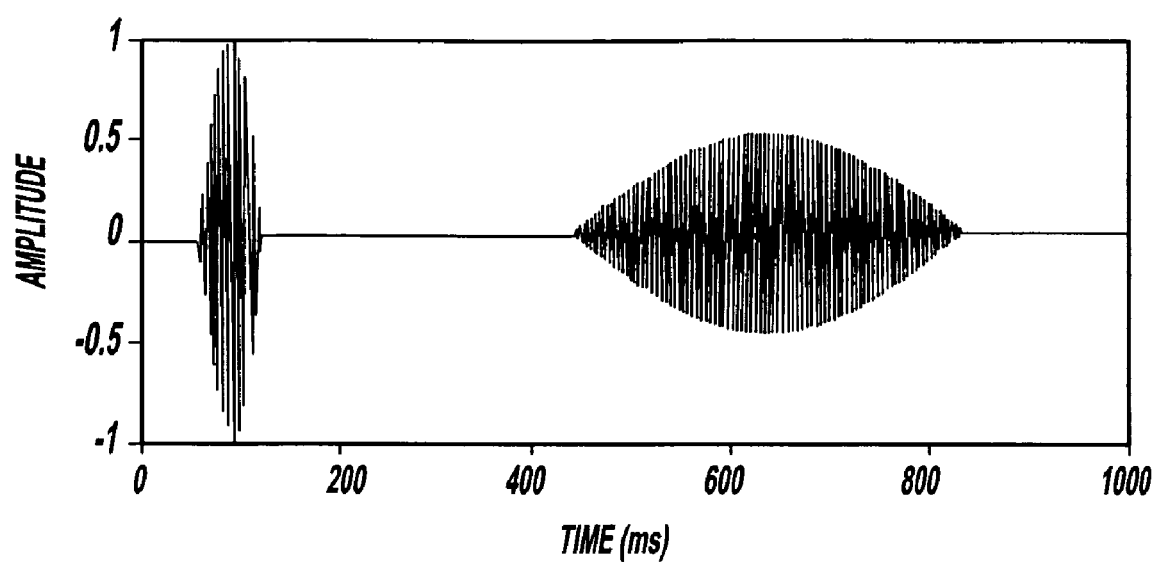
FIG. 19 is a graph with time on the horizontal axis and amplitude on the vertical axis showing an input excitation signal for the system shown in FIG. 9 that includes two pulses each with a favored envelope frequency.

FIG. 18 shows an excitation signal that has an increasing amplitude with a step at the beginning, where the total excitation signal is shown. A variation of the amplitude arises if the induced vibration has to be kept constant by a controller in case of a non-constant transient response of the transducer 94, an unstable coupling of the transducer 94, an unstable clamping condition, or if certain characteristics of the excitation signal, such as an exponential decrease, is intended. FIG. 19 shows an excitation signal that is a set of two pulses having a favored envelope frequency. The width of the first pulse is small which results in a small thermal diffusion length appropriate for detection of surface defects. The second pulse is substantially wider which results in a larger diffusion length appropriate for subsurface defects.

Various features of the object 92 can be tested, according to the invention, including the investigation of vibration modes, the performance of a tuned inspection, and the variation of the envelope of the excitation signal (intensity modulation). Investigation of the vibration modes can include performing a frequency sweep of the input signal for the determination of natural frequencies and a spatial pattern of eigen-modes of the object 92. Methods of measurement of the object 92 can include measurement of the phase shift between voltage and current and the effective electric power or vibration amplitude with an additional sensor.

For performance of a tuned inspection, variations of the frequency of the excitation signal can be provided. These variations in frequency include excitation of the object 92 with a set of frequencies, excitation of the object 92 with a frequency band, excitation of the object 92 with a noise signal, including a frequency band within the range of existing eigen-modes, and excitation of the object 92 with a chirp-signal. Repetition of the chirp-signal is possible by the repeated sweep of the frequency of the excitation signal up and down within a defined band where the eigen-modes exist. Performance of a tuned inspection of the amplitude of the excitation signals, includes providing the excitation signal with a stepped or varying amplitude pulse or set of pulses, excitation of the object 92 with continuously varying amplitudes in low-to-high or high-to-low in a swept manner, or excitation of the object 92 with continuously varying amplitudes in a cyclic, amplitude manner. Further, the locations of the vibration energy input based on the eigen-modes of the object 92 can be varied.

For the variation of the envelope of the excitation signal, the excitation signal can have a special signature of the envelope, such as recognition of the signature within the infrared response, such as discussed above for FIG. 16. Also, excitation of a signal that favors special frequencies of the envelope, including adaptation to the depth of a defect and thermal properties of the object 92 can be provided as discussed above for FIG. 19. These frequencies of the intensity modulation are typically some orders of magnitude lower than the sound frequency, as shown in FIG. 19. Also, an excitation signal that varies frequencies within the operational range can be provided or commercially available ultrasonic welding devices can be used in various ways. The frequency of the excitation signal can be varied, or swept, from low-to-high frequencies in the range. Alternately, the frequency of the excitation signal can be caused to vary in a cyclic manner from low-to-high, and from high-to-low, and repeated a number of times in a manner of frequency modulation.

The excitation signal can keep the vibrational energy transferred into the object 92 constant in order to balance changes of the coupling and clamping condition based on the measurement of vibration amplitude with an additional vibration sensor, or on the excitation signal using an IR response of the object 92 or from a reference sample. The excitation signal can have a steadily increasing amplitude, which stops or is subsequently kept constant, at a level below where damage is expected. The start of the signal should be at zero amplitude or at a safe amplitude.

According to another embodiment of the invention, variations of the defect detection test using a sequence of N number of excitations, where N is a pre-selected or automatically selected number of excitation pulses greater than one is provided. Each of the excitation pulses from 1 to N can be comprised of a pre-selected frequency, amplitude and duration, which is varied from excitation 1 to N in a manner that results in different eigen-mode vibrations in the object 92 during each excitation interval. The infrared or thermal imaging can remain active during the entire N-shot period of time so that defect heating events that are preferential to certain changing vibration conditions can be integrated or averaged over the entire test sequence.

The flexible excitation technique will maximize the opportunities for optimum vibration modes which cause a local heating at crack locations and minimizes arbitrary heating of the object 92 which could occur from excessive vibrations during nonlinear vibration mode changes. This combination of maximizing heating from defect locations and minimizing arbitrary or general heating of the object 92 will provide increased signal-to-noise ratio and aid in identifying indications of defects.

The system 90 can be designed for open-loop or closed-loop control. In the open-loop control embodiment, a tuned envelope excitation signal can be used to cause vibrations in the object 92 based on a predetermined eigen-mode analysis of the object 92, i.e., by analytical or empirical measurement methods. The predetermined eigen-modes are evaluated against the characteristics of the signal options, and one option is selected for use in the systems test cycle. The characteristics, i.e., frequencies, duration and amplitude, of the tuned or envelope excitation signal can be chosen to control the sensitivity of the test overall, control the levels of stress and strain induced in the object 92 by the vibrations relative to the level required to damage the object 92, control a limited area or areas of interest on the object 92, achieve an almost even distribution of vibration, or select modes that are determined to be effective at heating specific defects of interest for the inspection. In the case where the eigen-modes are not exactly known, however, the frequency band where they exist can be identified, and one or more choices of an excitation signal with a frequency band, noise signal or chirp-signal guarantees that one or more eigen-modes are excited.

In the closed-loop control embodiment, a tuned excitation signal can be used to vibrate the object 92. The actual vibrations induced in the object 92 are measured for the basis of eigen-mode analysis of the object 92. The analysis can be carried out by computing hardware or software analysis tools, and the results can be used by the thermography system 90 to select and control characteristics, i.e., frequencies, duration and amplitude, of the tuned or envelope excitation signal to induce the appropriate vibrations of the object 92. These characteristics can be chosen to control the sensitivity of the test overall, control the levels of stress and strain induced in the object 92 by the vibrations relative to the level required to damage the object 92, control the limited area or areas of interest on the object 92, achieve an almost even distribution of vibration, or select modes that are determined to be effective at heating specific defects of interest for the inspection.

Ultrasonic vibration exciter devices employing piezoelectric converters are available in the art that are commonly used for ultrasonic welding of plastics and other materials. These devices can be used for the transducer 94. The control system for these devices have some ability to vary frequency, amplitude, duration and contact force through limited ranges or can be modified internally or by the addition of an input signal conditioner to allow for flexible excitation. There are compact, low-cost ultrasonic vibration exciter devices, for example, piezoelectric, electromagnetic or magneto-strictive devices, that are available in the art to allow for flexible excitation in configurations using known transducing principles for generating signals. Examples of such devices are disclosed in U.S. Pat. Nos. 6,232,701 and 6,274,967. Also, the model F7-1 piezoelectric shaker system manufactured by Wilcox Research of Gaithersburg, Md. can be used. These devices combined with an arbitrary waveform generator, flexible function generator or digitally controlled signal generator, provide an appropriate power amplifier and microprocessor-based or computer-based control system that can be programmed to provide a flexible excitation signal for a vibration thermography system as required.

The availability of compact, low-cost ultrasonic vibration exciter devices also aids in the application of multiple exciter or arrays of exciters as another implementation. In other words, the transducer 94 can be replaced with a series of transducers or exciters. Additional flexibilities can be provided to customize the excitation modes by, for example, selecting combinations of exciter characteristics, including frequency, duration and amplitude, with eigen-mode features, such as nodes and anti-nodes at selected frequencies or combinations of frequencies and vibration modes to optimize the inspection results for selected areas of interest, types of defects and degradation to be indicated in situation variations in the object 92, such as results from manufacturing variations or from material aging or wear and degradation due to exposure to operational conditions of the object 92.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A defect detection system for detecting defects in a structure, said system comprising:
    a sound source for applying a sound input signal to the structure, said input signal including a plurality of frequency signals having different frequencies, said input signal heating the defects in the structure; and
    a thermal imaging camera for generating thermal images of the structure to identify the defects.

2. The system according to claim 1 wherein the input signal is a combination of two or more frequency signals centered at different frequencies.

3. The system according to claim 1 wherein the input signal has a Gaussian frequency band.

4. The system according to claim 1 wherein the input signal is a chirp-signal whose frequency changes in time.

5. The system according to claim 1 wherein the input signal is a signature signal having a set of pseudo-random pulses.

6. The system according to claim 1 wherein the input signal has an increasing, decreasing or constant amplitude in various sequential combination, including optionally steps in amplitude.

7. The system according to claim 1 wherein the input signal is based on a rectangular frequency band.

8. The system according to claim 1 wherein the input signal is a favored envelope frequency including one pulse having a small pulse width and another pulse having a larger pulse width for detection of defects in different depths.

9. The system according to claim 1 wherein the sound source is selected from the group consisting of EMATs, ultrasonic vibrators, piezoelectric vibrators, electro-magnetic vibrators and magneto-strictive vibrators.

10. The system according to claim 1 further comprising a signal shaper, said signal shaper generating the input signal to have a predetermined duration, amplitude and frequency.

11. The system according to claim 1 wherein the sound source is a broad-band transducer capable of providing a broad-band frequency signal.

12. The system according to claim 1 wherein the sound source includes a plurality of transducers each being tuned to a different narrow band center frequency.

13. The system according to claim 1 further comprising a vibration sensor coupled to the structure, said vibration sensor sensing vibrations in the structure.

14. The system according to claim 13 wherein the vibration sensor is selected from the group consisting of an eddy current based vibration sensor, an accelerometer, an optical vibration sensor, a microphone, an ultrasonic transducer and an ultrasonic vibration sensor.

15. The system according to claim 13 wherein the vibration sensor measures a phase shift between current and voltage of the sensed vibrations to determine the natural frequencies of the structure.

16. The system according to claim 13 wherein the vibration sensor measures an amplitude characteristic of current or voltage of the sensed vibrations to determine the natural frequencies of the structure.

17. The system according to claim 1 wherein the input signal is a tuned excitation signal that provides an open-loop or a closed loop control.

18. A defect detection system for detecting defects in a structure, said system comprising:
    a sound source for applying a sound input signal to the structure, said input signal having one or more frequencies or a single frequency signal with an amplitude modulation selected to be at or near an eigen-mode of the structure or selected to avoid the eigen-mode of the structure, said input signal heating the defects in the structure; and
    a thermal imaging camera for generating thermal images of the structure to identify the defects.

19. The system according to claim 18 wherein the input signal is selected from the group of input signals consisting of an input signal having a combination of two or more frequency signals centered at different frequencies, an input signal that has a Gaussian frequency band, an input signal that is a chirp-signal, an input signal that is a signature signal having a set of random pulses, an input signal that has a rectangular frequency band, an input signal that has an increasing amplitude with a step, and an input signal that includes one pulse having a short pulse duration and another pulse having a wide pulse duration for detection of defects in different depths.

20. A defect detection system for detecting defects in a structure, said system comprising:
    a sound source for applying a sound input signal to the structure, said input signal being a single frequency signal with an amplitude modulation, wherein the amplitude modulation provides a stepped or varying amplitude modulated signal, said input signal heating the defects in the structure; and
    a thermal imaging camera for generating thermal images of the structure to identify the defects.

* * * * *